(12) United States Patent
Richter (10) Patent No.: US 10,143,563 B2
(45) Date of Patent: Dec. 4, 2018

(54) IMPLANT FOR SEALING A DEFECT IN THE ANULUS FIBROSUS OF AN INTERVERTEBRAL DISC

(71) Applicant: Marcus Richter, Wiesbaden (DE)

(72) Inventor: Marcus Richter, Wiesbaden (DE)

( * ) Notice: Subject to any disclaimer, the term of this patent is extended or adjusted under 35 U.S.C. 154(b) by 0 days.

(21) Appl. No.: 15/749,719

(22) PCT Filed: Aug. 3, 2016

(86) PCT No.: PCT/EP2016/068579
§ 371 (c)(1),
(2) Date: Feb. 1, 2018

(87) PCT Pub. No.: WO2017/021467
PCT Pub. Date: Feb. 9, 2017

(65) Prior Publication Data
US 2018/0214278 A1    Aug. 2, 2018

(30) Foreign Application Priority Data

Aug. 4, 2015    (DE) .................. 10 2015 112 799

(51) Int. Cl.
*A61F 2/44*    (2006.01)
*A61F 2/46*    (2006.01)
(Continued)

(52) U.S. Cl.
CPC ............ *A61F 2/442* (2013.01); *A61F 2/4611* (2013.01); *A61B 17/86* (2013.01); *A61F 2/4614* (2013.01);
(Continued)

(58) Field of Classification Search
CPC ...... A61F 2/442; A61F 2/4611; A61F 2/4614; A61F 2002/2835; A61F 2002/4435; A61F 2002/464; A61F 2220/0041; A61B 17/86
(Continued)

(56) References Cited

U.S. PATENT DOCUMENTS

| 2004/0111161 A1 | 6/2004 | Trieu | |
| 2005/0234557 A1* | 10/2005 | Lambrecht | .......... A61B 5/1076 623/17.16 |

(Continued)

FOREIGN PATENT DOCUMENTS

| CN | 102036613 A | 4/2011 |
| CN | 102341047 A | 2/2012 |

(Continued)

OTHER PUBLICATIONS

International Search Report and Written Opionion, PCT/EP2016/068579; dated Nov. 11, 2016.
(Continued)

*Primary Examiner* — Pedro Philogene
*Assistant Examiner* — David C Comstock
(74) *Attorney, Agent, or Firm* — Knobbe, Martens, Olson & Bear, LLP (57) ABSTRACT

The invention relates to an implant (1) for sealing a defect (7c) in the annulus fibrosus (7a) of an intervertebral disc (7), comprising a retaining portion (3) for introducing into the defect (7c), a flexible sealing element which is connected to an inner end of the retaining portion, and a securing element (2) which is connected to the outer end of the retaining portion and which can be fixed to a vertebra (8) adjoining the intervertebral disc in order to hold the retaining portion (3) in a fixed position. According to the invention, this is achieved in that a securing limb (2), which is angled relative to the longitudinal axis of the retaining portion, is arranged on the outer end of the retaining portion (3), said securing limb being designed for laterally contacting a bony structure of a vertebra adjacent to the intervertebral disc and being securable on the vertebra by means of a fixing element which can be moved relative to the securing limb. The sealing element has inner reinforcements.

20 Claims, 7 Drawing Sheets

(51) Int. Cl.
*A61B 17/86* (2006.01)
*A61F 2/28* (2006.01)

(52) U.S. Cl.
CPC ............... *A61F 2002/2835* (2013.01); *A61F 2002/4435* (2013.01); *A61F 2002/464* (2013.01); *A61F 2220/0041* (2013.01)

(58) Field of Classification Search
USPC ....................................................... 623/17.16
See application file for complete search history.

(56) References Cited

U.S. PATENT DOCUMENTS

| | | |
|---|---|---|
| 2007/1067040 | 3/2007 | Ferree |
| 2007/0100354 A1 | 5/2007 | Cauthen, III et al. |
| 2011/0153022 A1* | 6/2011 | Singhatat ............... A61F 2/441 623/17.16 |
| 2012/0010653 A1 | 1/2012 | Seifert et al. |
| 2012/0116516 A1* | 5/2012 | Aflatoon ............... A61F 2/442 623/17.16 |

FOREIGN PATENT DOCUMENTS

| | | |
|---|---|---|
| JP | 2007-515988 | 6/2007 |
| JP | 2008-514372 | 5/2008 |
| WO | WO 2007/078978 | 7/2007 |

OTHER PUBLICATIONS

International Preliminary Report on Patentability Chapter II, dated Nov. 7, 2017.
Office Action for Japanese Application No. 2018-516552, which is the counterpart Japanese national phase application of the present US national phase application.
Chinese Office Action for Chinese Application No. 201680045945.2 dated Jul. 31, 2018 which is the counterpart Chinese national phase application of the present US national phase application.

* cited by examiner

IMPLANT FOR SEALING A DEFECT IN THE ANULUS FIBROSUS OF AN INTERVERTEBRAL DISC

TECHNICAL BACKGROUND

The present invention relates to an implant for sealing a defect in the anulus fibrosus of an intervertebral disc, with a retaining portion for insertion into the defect, a sealing element connected to an inner end of the retaining portion and a securing element, connected to the outer end of the retaining portion, which can be fixed to a vertebra adjoining the intervertebral disc, in order to hold the retaining portion in a fixed position, wherein the flexible sealing element has a reduced projected area in a top view from the front along the longitudinal axis of the retaining portion in a first state and has a widened projected area, which is at least twice the reduced projected area, in a second state.

Intervertebral discs consist of two parts: an outer anulus fibrosus (fibrous ring) and an inner nucleus pulposus (jelly-like core). The anulus fibrosus consists of concentric layers of collagen fibres of connective tissue (outer zone), which gradually pass inwardly into fibrous cartilage (inner zone) and surround the nucleus pulposus. The nucleus pulposus is a jelly-like tissue with few cells and with a high water content. It acts in a shock-absorbing manner like a water cushion and absorbs shocks during movement of the spinal column. The intervertebral disc arranged between two vertebrae delimits the distance between the end plates of these vertebrae and, as an elastically deformable damping element, also supports the mobility of the spinal column. The cover plates or end plates, adjoining the intervertebral disc above and below, of the neighbouring vertebrae delimit the so-called intervertebral disc space.

Within the framework of the degeneration of the intervertebral disc that cannot be avoided with increasing age, defects in the form of a tearing or bursting open of the anulus fibrosus often occur. Through such a defect, parts of the nucleus pulposus can escape from the intervertebral disc, which is usually called a herniated disc.

The nucleus pulposus escaping through the defect can, in particular if it escapes dorsally in the direction of the spinal canal of the spinal column, press on neural structures. If this leads to neurological deficits and/or pain, surgery may become necessary. In the event of such surgery, the escaping parts of the nucleus pulposus are removed. However, the defect in the anulus fibrosus is not yet sealed thereby. Specifically, the anulus fibrosus has a hole or a wider or narrower interruption, wherein parts of the jelly-like intervertebral disc core can continue to escape and can lead to discomfort again. Within the framework of a first emergency treatment or for a better introduction of the retaining portion and the sealing element, the defect can also be surgically widened and/or prepared.

In order to durably seal a defect in the anulus fibrosus of an intervertebral disc and to prevent the nucleus pulposus from escaping, the implants defined at the beginning, among other things, are used. The known implant for sealing a defect in the anulus fibrosus of an intervertebral disc, such as is described e.g. in WO 2007/078978 A2, has a retaining portion with a bone anchor which can be fixed to the adjoining vertebra. The retaining portion is inserted into the defect with its inner end and the sealing element secured thereto at the front. The reduced projected area of the sealing element onto a surface perpendicular to the longitudinal axis of the retaining portion allows it to be guided through the defect along this longitudinal axis. The outer end of the retaining portion then terminates more or less flush with the outer side of the anulus fibrosus. The sealing element has the form of a flap, attached to the inner end of the retaining portion, which is to be unfolded after introduction through the anulus fibrosus and is then to seal the entire free defect cross section from the inner side of the anulus fibrosus. The bone anchor is inserted into the intervertebral disc space and is thus anchored in the cover or end plate of an adjoining vertebra in order thus to fix the implant to the vertebra.

The flap of the implant to be laid against the inner wall of the anulus fibrosus according to WO 2007/078978 A2 has to be folded in a first state and has to lie in front of and/or next to the retaining portion in this first state. In the top view from the front along the longitudinal axis of the retaining portion, the sealing element, in the first state, thus has a small cross-sectional area (=projected area onto a plane perpendicular to the longitudinal axis of the retaining portion) and, in this state, can be inserted into the inside of the intervertebral disc through the opening in the anulus fibrosus forming the defect. In a second state, the sealing element is unfolded and rests against the inner side of the anulus fibrosus, wherein it is to cover and seal the defect completely. In this state, the cross-sectional or projected area of the sealing element, seen along the axis of the retaining portion, is typically at least twice as large as in the first state.

The mentioned longitudinal axis of the retaining portion is substantially defined by the direction of insertion of this portion into an opening which is in turn determined by the geometry of the retaining portion and the elements arranged thereon. The longitudinal axis can also be defined as the connection of the outer and inner ends of the retaining portion.

The implant according to WO 2007/078978 A2 above all has the disadvantage that the flap which can theoretically be laid against the inner wall of the anulus fibrosus can be spread out into the desired position only with difficulty or not at all, and that the pressure inside the intervertebral disc displaces this flap and presses it outwards through the defect again.

Furthermore, the intervertebral disc gradually loses volume due to the escape of the nucleus pulposus, but also as a result of aging, and a pressure drop in the intervertebral disc occurs. The height of the intervertebral disc decreases, and thus also the height of the intervertebral disc space. The bone anchor of WO 2007/078978 A2 arranged in the intervertebral disc space can therefore damage the adjoining end plates in the event of an almost inevitable degeneration of the intervertebral disc and cause additional mobility restrictions. The bone anchor durably remaining in the intervertebral disc space can also make interbody fusion at a later time, for example with "cages" (ALIF, TLIF, PLIF, XLIF), more difficult.

OBJECT OF THE INVENTION

Against this background, the object of the present invention is to provide an implant for sealing a defect in the anulus fibrosus of an intervertebral disc which guarantees a secure seat in the defect and securely prevents the nucleus pulposus from escaping.

SUMMARY OF THE INVENTION

For an implant described at the beginning for sealing a defect in the anulus fibrosus of an intervertebral disc, this object is at least partially achieved in that a securing limb angled relative to the retaining portion is arranged on the outer end of the retaining portion, which securing limb is designed to be secured to a bony structure of a vertebra neighbouring the intervertebral disc and can be secured to the vertebra with the aid of a fixing element which is movable relative to the securing limb, wherein the flexible sealing element is at least partially elastically deformable and pretensioned in the direction of the unfolded state and/or has internal reinforcements to actively unfold the sealing element.

Unless otherwise indicated by the context, within the framework of the present description the terms "outer" and "inner" are clearly used such that an "inner side" of the implant is always the side facing the centre of the intervertebral disc or of an adjoining vertebra during or after the insertion of the implant, while the "outer side" is the side facing away from the intervertebral disc or the vertebra.

To insert the implant, the retaining portion is inserted into the defect of the anulus fibrosus (optionally prepared with clean edges) with its inner end at the front, until the securing limb arranged angled on the outer end of the retaining portion rests against an adjoining vertebra, preferably against its outer side. The flexible sealing element provided on the inner (front) end of the retaining portion is then brought into its second state, with enlarged cross-sectional area, on the inner side of the anulus fibrosus transverse to the longitudinal direction of the retaining portion, in order to cover the cross section of the defect.

The widening of the cross-sectional area either happens automatically, in that the flexible sealing element is first folded, so that it can be inserted into the inside of the intervertebral discs through the defect at the front end of the retaining portion, and the sealing element elastically under pretension unfolds as soon as it is released, or is actively brought about by internal reinforcing elements and with the aid of external actuation elements which are connected to the reinforcements of the sealing element. In both cases, a sufficiently dimensionally stable unfolded state of the sealing element is achieved which prevents the sealing element or parts thereof from being pressed out through the defect opening. A characteristic of the present invention is thus that the sealing element is designed such that it can adopt a folded state in which it can be inserted into the inside of an intervertebral disc through the defect and an unfolded or spread-out state which is stable. The means for this are a sufficiently stiff but still elastically deformable material and/or corresponding reinforcements and stiffeners of the sealing element.

As a sealing element attached to the front or inner end of the retaining portion which points away from the securing limb, a fothering that can be spread out is preferably arranged, which is guided into the inside of the intervertebral disc through the defect and can be laid against the inner side of the anulus fibrosus after being unfolded or spread out.

In its spread-out state, the fothering protrudes, in a top view onto the front end face of the retaining portion, beyond the cross-sectional area of the retaining portion at least on two opposite sides and preferably also in a third direction (upwards or downwards) and seals the defect or the inner opening of the defect in the anulus fibrosus. The fothering is dimensioned such that it typically projects clearly beyond the edges of a typical defect in all directions and in particular in the plane of the intervertebral disc and preferably also in a direction perpendicular thereto, and rests around the defect extensively on the inner side of the anulus fibrosus. In other words, in a top view onto the front end of the retaining portion, the projected area of the sealing element (onto the plane perpendicular to the direction of view) is at least twice the reduced projected area which the sealing element has during introduction through the defect.

So that it takes quickly and better, the fothering can be coated with or produced from a material that promotes cell growth. The retaining portion and also the securing limb can be produced from a material that can be resorbed by the body, they maintain their retaining and fixing function for the sealing element until the sealing element is fixedly adhered to the intervertebral disc.

The implant and its fothering can be provided, as required, in different sizes and designs, wherein however the dimensions and shapes are expediently chosen such that they each cover a large range of application cases.

The securing limb, extending angled relative to the retaining portion, which rests with its inner side against an adjoining vertebra, is secured to the vertebra, before or after the fothering is spread out, with the aid of the connection means.

The length of the retaining portion typically lies between approximately 3 and 8 mm, the securing limb typically has a length of between approximately 5 and 15 mm, wherein the dimensions used depend on the anatomy and size of the respective patients and, as a result, a corresponding set of implants of different sizes is logically made available to the surgeon. It can also be expedient if securing limb and retaining portion are connected to each other in a detachable and possibly also articulated manner, with the result that different securing limbs and retaining portions can be combined with each other. It is understood that a detachable articulated connection between securing limb and retaining portion is ensured such that this connection cannot loosen automatically in the case of an inserted implant.

A fothering provided according to an embodiment is initially closed or folded for introduction into the interior of an intervertebral disc through a defect in the anulus fibrosus and not spread out until it has been introduced into the interior of the intervertebral disc. A fothering is a flat, flexible article such as, for example, a membrane, a cloth or a flap. The intervertebral disc internal pressure helps to press the fothering, once spread out, from the inside of the intervertebral disc against the anulus fibrosus. The reinforcements, which are internal or integrated into the fothering, ensure that the fothering is not pushed together into itself and pressed out through the defect opening by the pressure prevailing in the intervertebral disc. The spread-out fothering completely covers the inner opening of the defect in the anulus fibrosus and rests flat on the inner side of the anulus fibrosus. Because of the fixing by securing limb and retaining portion and due to the internal reinforcements or stiffeners of the fothering, the fothering durably holds its position and can thus fixedly adhere to the anulus fibrosus within a relatively short time. Retaining portion and securing limb are then no longer needed. They could therefore, just as the fixing element would also, consist directly of a material that can be slowly resorbed by the body of a patient. Corresponding, suitable materials are, for example, polylactide or iron-tricalcium phosphate.

In an embodiment, the fothering is produced from PTFE. The internal reinforcements of the fothering, which do not come into contact with body tissue (the intervertebral disc material), can consist of an elastic and stable metallic material, e.g. of spring steel or a titanium alloy wire.

In an embodiment of the invention, at least the side of the fothering which faces the anulus fibrosus in the spread-out state of the fothering has bioactive substances, such as for example growth factors, cell adhesion promoters and antibacterial coatings, such as are also used, for example, in other areas of bone surgery. For this, the surface of the fothering can be deliberately roughened or porous. The bioactive substances have the effect that the fothering adheres to the anulus fibrosus or takes more quickly and more easily, and thus forms a fixed connection to the anulus fibrosus.

In an embodiment, the fothering has several segments in the form of flaps or bulges, which are connected to each other and/or overlap in portions in a spread-out state of the fothering. A one-piece fothering can have several flaps or bulges and individual flaps or segments of the fothering can also be delimited from each other by seam, fold and/or stitch lines. In an embodiment, several segments are assembled into a fothering, wherein neighbouring segments are glued, stitched, welded and/or woven to each other. The shape and extent of the individual flaps of the fothering are targeted at the anatomical conditions. In every case, the fothering is to protrude at least partially beyond the cross section of the retaining portion and in particular also beyond the cross section of a typical defect in the anulus fibrosus, wherein these cross sections almost match at least in the preferred embodiment. For this, retaining portions with different (typical) cross sections can be provided.

In an embodiment, the fothering comprises two segments which, in a top view onto the inner side of the retaining portion, extend beyond the cross section of the retaining portion on opposite sides in a spread-out state of the fothering, and span the defect in the intervertebral disc preferably over its entire height or thickness.

In another embodiment, the fothering has at least three or four segments preferably extending in the shape of a star from the retaining portion, wherein neighbouring segments are preferably connected to each other and/or overlap in a spread-out state of the fothering.

In a further embodiment, some segments or all segments of the fothering are designed leaf-shaped. Examples are represented in the figures.

Metallic and/or non-metallic reinforcements inside the fothering are preferably elastically pretensionable and provide a force for spreading out the fothering. The thus-pretensioned, folded fothering can open automatically after insertion into the intervertebral disc or support a spreading-out by additional actuation means, such as are yet to be described below. For example, the reinforcements can be metal wires and/or reinforced fibres incorporated into the material of the fothering or connected to the fothering.

In an embodiment, an actuation means, preferably a pulling means, which is connected to the fothering or its segments such that the fothering can be spread out with the aid of the actuation means, is guided through the retaining portion from its outer to its inner end. The defect in the anulus fibrosus can be sealed by spreading out the fothering.

In an embodiment, the fothering has an umbrella mechanism. In the case of an umbrella mechanism, the fothering or some or all segments have a preferably rib-like reinforcement which is connected to one or more struts, as well as an articulated connection to a pull rod which is connected to the fothering.

In a further embodiment, a wire or a pull thread is provided which is connected to the fothering or its segments, with the result that either the fothering is actively unfolded by pulling on the wire or thread or a pretensioned fothering is released in order to unfold automatically.

According to an embodiment, the securing element here is formed as a securing limb, arranged on the outer end of the retaining portion, which, in contrast to the above-discussed state of the art, is not inserted into the intervertebral disc space, but extends from the outer end of the retaining portion angled such that it can rest externally against a vertebra.

In an embodiment of the invention, the securing limb and the retaining portion are formed as one piece at a fixed angle to each other. In an alternative embodiment, the angle between retaining portion and securing limb can be variable stepwise or steplessly, and in particular the securing limb can be connected in an articulated manner to the outer end of the retaining portion. In the implanted state, the angling of the securing limb relative to the retaining portion is typically between 60 and 110 degrees, wherein the angle between the direction of insertion of the retaining portion from its outer to its inner end and the direction defined by the connection of the securing limb at the outer end of the retaining portion to the free end of the securing limb is to be measured.

The retaining portion can, for example, have a basic shape in the form of a rectangular box, cylinder, rod or ellipsoid and is angled relative to the securing limb. The length of the retaining portion between the securing limb and the lug of the sealing element on the inner end of the retaining portion corresponds at least to the typical thickness of an anulus fibrosus (e.g. approximately 5 mm). In an embodiment, the retaining portion is made in one piece with the securing limb.

The retaining portion can optionally also be an elastically or sometimes also plastically deformable article, e.g. a hollow article, in order to be able to adapt to a decreasing height of the intervertebral disc space in the event of further degeneration of the intervertebral disc.

In order that, when used as intended, the implant is held in its position and orientation relative to the intervertebral disc by the fixing to a circumferential surface of the neighbouring vertebra, the securing limb is designed to be laid laterally against a bony structure of a vertebra adjoining the intervertebral disc to be sealed and secured thereto by means of a separate fixing element.

According to an embodiment, at a distance from the retaining portion, the securing limb has a cross hole for a fixing element, to be anchored in the vertebra, to be guided through.

The fixing element produces the fixed connection of the securing limb to the bony structure of the adjoining vertebra. In this way, a fixing element or bone anchor inserted into the intervertebral disc space can be dispensed with and further damage to the end plate of the vertebra in the event of progressive degeneration of the intervertebral disc can be avoided.

In the simplest case, the fixing element consists of a nail or a screw which, optionally with the aid of an expansion anchor, is secured in the vertebra and extends through the matching cross hole in the securing limb resting laterally to or against the circumferential surface of the vertebra, in order thus to fix the securing limb to the vertebra.

The fixing element is movable (for example rotatable) separately from the securing limb. However, in an embodiment, it can be captively attached to the securing limb. The fixing element can additionally be secured against loosening from a bone structure, including for example by means of an anti-twist device in the case of a screw or a screw anchor.

In an embodiment, the cross hole can be inclined at an angle in the range of from 0° to 30° relative to the longitudinal direction of the retaining portion—independently of the angling of the securing limb relative to the retaining portion—wherein the direction of this inclination can be different depending on the precise location of the defect and the respective anatomical conditions. A cross hole inclined relative to the securing limb can make it easier to handle the implant, if the securing limb is more achievable at a particular angle relative to the securing limb because of anatomical conditions, as a corresponding fixing element or a securing screw also runs inclined due to the angle of inclination of the cross hole and corresponding instruments for producing the connection of the implant to the vertebra can be inserted into the patient's body at the same angle of inclination, in order thus to reduce or completely prevent the otherwise inevitable injury to spinal processes or other skeletal parts or soft tissue.

The securing limb can consist, for example, of a short bar, a plate or a strip which extends transverse to the longitudinal axis of the retaining portion. The retaining portion and the securing element can, together, have an L shape, wherein one limb of the L shape can be laid against a vertebra and the retaining portion forming the second limb can be inserted into the defect of the anulus fibrosus. It is understood that the size and shape of the securing limb are chosen such that the retaining portion can be substantially completely inserted into the anulus fibrosus, while at the same time the area of the securing limb having the cross hole can be laid laterally against the circumferential surface of a vertebra adjoining the intervertebral disc.

The terms of the securing limb extending "transverse" to the retaining portion, or of the implant forming an "L shape", here comprise not only embodiments in which the retaining portion and the securing limb extend exactly perpendicular to each other from a common connection area, but also those in which the two limbs of the L shape (retaining portion and securing limb) form any angle between 60° and 110° with each other.

In an embodiment, an adapter sleeve is provided which can preferably be received in the cross hole in different alignments and which itself has a hole, the axis of which (after insertion of the adapter sleeve) is inclined at an angle in the range of from 0° to 30° relative to the longitudinal axis of the cross hole. With the aid of such an adapter sleeve, it is possible to vary the direction of inclination of the hole for receiving the fixing element relative to the securing limb and to the retaining portion even subsequently. For the secure transmission of force from the fixing element to the securing limb, the cross hole in the securing limb can, for example, be formed as a stepped hole and the outer surface of the adapter sleeve can be formed correspondingly stepwise and means can additionally be provided to fix the adapter sleeve in different orientations with respect to the axis of the cross hole.

Optionally, the adapter sleeve can be fixedly pre-installable in the cross hole in a desired alignment.

In yet another embodiment, the retaining portion has a hole extending in the longitudinal direction from outside to inside through it and optionally also through a portion of the securing limb, which hole is sealed by a septum or a plug made of elastic material and acts as an application port. Through such a plug, with the aid of a hypodermic needle which is pushed through the elastic material of the plug, for therapeutic and/or diagnostic purposes, fluids can be introduced into the inside of the intervertebral disc or drawn out of the inside of the intervertebral disc, without damaging the anulus fibrosus further or having to remove the implant again altogether. The elastic material ensures that the channel in the septum or plug generated by the hypodermic needle immediately seals itself again when the needle is withdrawn. The hole preferably extends in a straight line through the retaining portion and, where necessary, through the securing limb. The material of the application port is preferably to be selected such that, after a suitable hollow needle has pierced it and been withdrawn again, the feed channel in the material created during the piercing seals itself again completely and securely. In an embodiment, the application port is produced from silicone.

In the case of a defect of the anulus fibrosus, a part of the nucleus pulposus responsible for the internal pressure and the damping function of the intervertebral disc usually escapes and also cannot be readily filled in during the surgical correction of the defect, for example before or during the insertion of the implant according to the invention. The closure of the defect must heal first and foremost, or the sealing elements of the implant must adhere to the anulus fibrosus, in order to guarantee a sufficient seal against a renewed escape of nucleus pulposus or a replacement under the high pressures and the associated forces which act in the intervertebral disc. On the other hand, it would be advantageous to refill the intervertebral disc that has been at least partially emptied of nucleus pulposus, in order that the intervertebral disc can fulfill its damping function again as completely as possible. Here, it can be advantageous to use the application port in the implant according to the invention to fill the anulus fibrosus with a replacement for nucleus pulposus after the defect has been sealed and the closure has healed or adhered sufficiently, which can indeed be the case only weeks or months after the surgical procedure to seal the defect. The replacement can be any desired means suitable for such purposes, for example the body's own cell cultures or also another means for regenerating the nucleus pulposus. The replacement is introduced into the intervertebral disc space by means of a hypodermic needle to be pushed through the application port. In addition to or instead of replacements, of course, other substances can also be introduced, for example pharmaceutically active substances, such as antibiotics, which can also be introduced immediately after the surgical insertion of the implant, in order to prevent a post-operative infection.

The retaining portion and/or the securing limb of the implant or parts thereof can consist of a resorbable material, preferably polylactide or iron-tricalcium phosphate. Resorbable materials make it possible to use the implant even if the height of the intervertebral disc space is small and avoid damage to the adjoining vertebral end plates.

BRIEF DESCRIPTION OF THE DRAWINGS

Further advantages, features and possible applications of the present invention will become clear with reference to the following description of preferred embodiments and the associated figures. There are shown in.

All figures are only of a schematic nature with regard to dimensions and dimensional ratios and the precise outline shapes. In particular, sharp edges and transitions in the embodiments represented can in reality be shaped differently and e.g. rounded.

DETAILED DESCRIPTION

Figure 1:
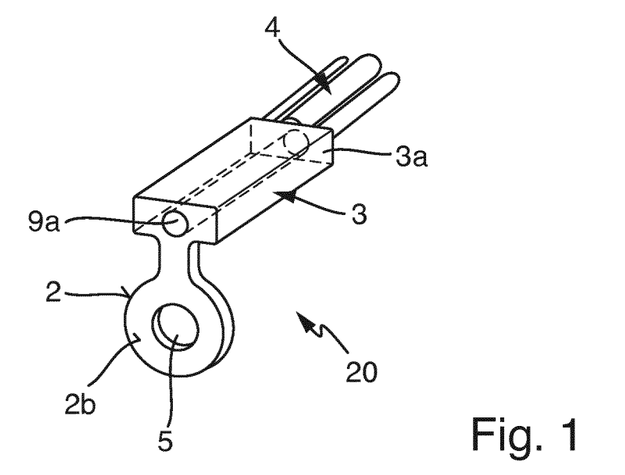
FIG. 1: a schematic, perspective view of an implant according to an embodiment of the present invention.

A perspective view of an implant 1 according to an embodiment of the invention is represented in FIG. 1. In a side view, the implant 1 has an L-shaped article 20 with a securing limb 2 which has a continuous hole 5 as well as an inner side 2a (not visible in FIG. 1) and, opposite this, an outer side 2b. The other limb of the L-shaped article 20 forms the retaining portion 3, which is designed for insertion into a defect in the anulus fibrosus of an intervertebral disc. A fothering 4 that can be spread out, which is indicated in its closed, folded state in FIG. 1, is arranged on the inner end 3a of the retaining portion 3. The retaining portion 3 can have a central longitudinal hole 9a for receiving a plug, not represented here.

The hole 5 for receiving a fixing element 6 (not represented in FIG. 1), which extends through the securing limb 2 from the outer side 2b to the inner side 2a and, in the implanted state, into an adjoining vertebra, extends in an area, spaced apart from the retaining portion 3, of the securing limb 2 which is designed to be laid with its inner side 2a laterally against a bony structure of a vertebra neighbouring the intervertebral disc to be sealed, more precisely against its circumferential surface.

Figure 2:
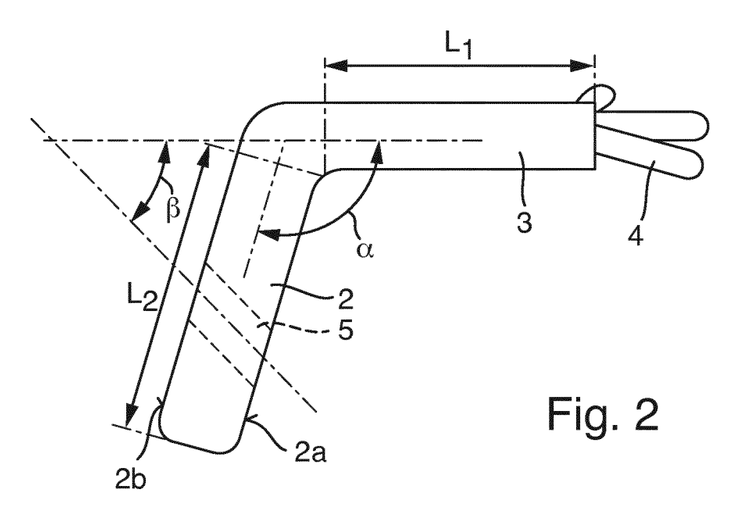
FIG. 2: a side view of the implant according to the invention according to FIG. 1.

FIG. 2 shows an implant in a side view, with reference to which different characteristics and dimensions of the implant can be explained. The angle between the longitudinal extent of the retaining portion and the longitudinal extent of the securing limb 2 is designated α and can be between 70 and 130 degrees. The angle β between the axis of the hole 5 and the longitudinal extent of the retaining portion 2 is independent of the angle α and can adopt e.g. values between 0 and 60 degrees.

Figure 3:
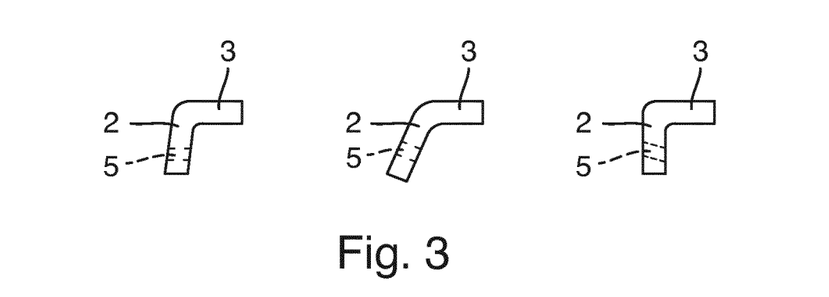
FIG. 3: different variants of the arrangement of retaining portions and securing limb.
Figure 4:
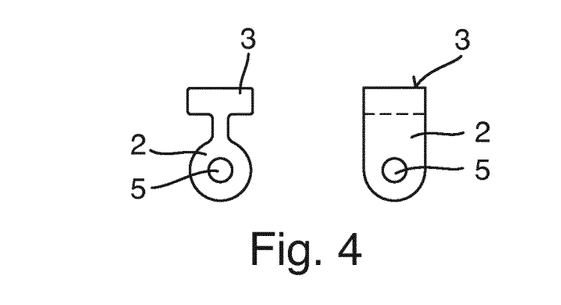
FIG. 4: two variants of securing limbs.

FIGS. 3 and 4 show side and rearward (from the outer side 2b) views of different variations of retaining elements 3 and securing limbs 2. As can be seen, the angle α between securing limb 2 and retaining portion 3 can vary and the angle β of the axis of the hole 5 relative to the securing limb 2 or to the retaining portion 3 can also vary and does not necessarily run parallel to the longitudinal direction of the retaining portion 3.

FIG. 4 is a top view from outside along the longitudinal axis of the retaining portion which substantially corresponds to the direction of insertion of the retaining portion into the defect 7c. It can be seen that the securing limb 2 can adopt different shapes, wherein it substantially depends on its possible positioning on a vertebra 8 and the fixing thereto, which is preferably realized here with the aid of a hole 5 and fixing elements 6 extending through this.

The length L1 of the retaining portion 3 typically lies between 3 and 10 mm and the length L2 of the securing limb 2 also lies in this order of magnitude or slightly above it. The size of the securing limb 2 is dimensioned in particular such that, at a distance from the end plate of the vertebra adjoining the intervertebral disc, it has securing elements, in this case in the form of the hole 5 and for example a screw 6 with a screw anchor 16, as represented in FIG. 5.

Figure 5:
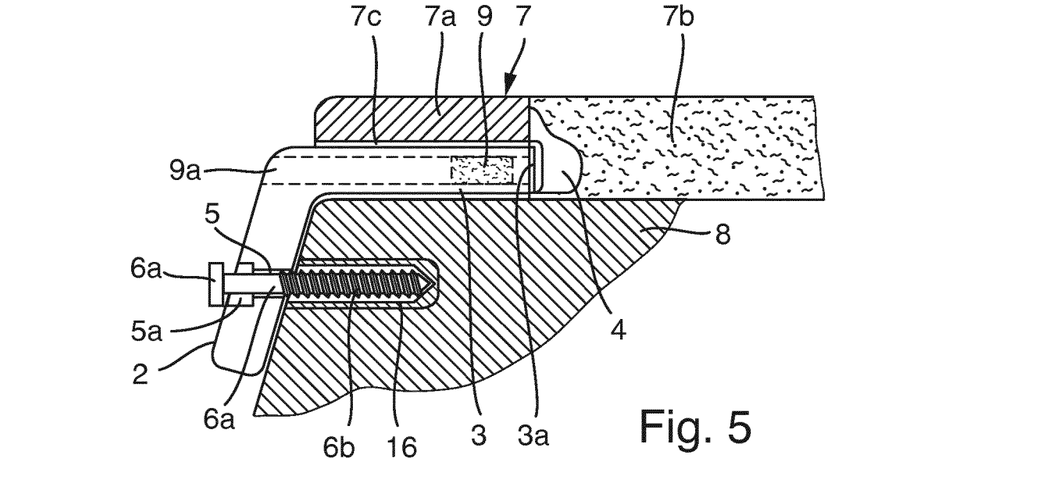
FIG. 5: a longitudinal section through an intervertebral disc with an implant according to the invention according to FIG. 1.

FIG. 5 shows a similar embodiment in a schematically represented state inserted into an intervertebral disc 7 in a cross section through the intervertebral disc 7 perpendicular to its plane in the area of a defect 7c.

The intervertebral disc 7 indicated has a defect 7c, through which the nucleus pulposus 7b can escape, in its anulus fibrosus 7a. The retaining portion 3 is inserted into the defect 7c to seal the defect 7c. The retaining portion 3 and also the folded fothering 4 in every case have a smaller cross section than the defect 7c, in order that the retaining portion 3 can be inserted into the defect 7c with the folded fothering 4 at the front. The fothering 4 in its unfolded or spread-out state is represented on the inner end 3a of the retaining portion 3. In the spread-out state, the fothering 4 nestles up against the anulus fibrosus from the inside and thus seals the defect 7c in the anulus fibrosus 7a. The intervertebral disc internal pressure prevailing in the jelly-like substance of the nucleus pulposus 7b presses the fothering 4 against the anulus fibrosus 7a from the inside.

In its spread-out state and in a top view onto the inner end of the retaining portion 3, the fothering 4 extends clearly beyond the cross-sectional area of the retaining portion 3 and also well beyond the cross section of the defect 7c. In this way the fothering 4 can adhere extensively to the intervertebral disc and take, and thus also has a good hold in the intervertebral disc 7. The retaining portion 3 and also the securing limb 2 are then no longer needed and can therefore also consist of a material that can be gradually resorbed by the human body, such as for example polylactide or iron-tricalcium phosphate.

As can be seen in the view according to FIG. 5, the area of the securing limb 2 designed to be laid laterally against a bony structure of a neighbouring vertebra 8 has a hole or through hole 5 for receiving a screw 6. The hole 5 extends from the outer side 2b of the securing limb 2 to the inner side 2a and also has a stepwise widening 5a on the outer side for receiving a screw head 6a. The fixing element here is thus a screw, which has a head portion 6a and a threaded portion 6b. The head portion 6a is received in the stepwise widening 5a, while the threaded portion 6b of the fixing element is screwed into the bone of the vertebra 8, specifically into an expansion anchor 9 in a hole introduced into the vertebra 8.

Through this lateral securing of the implant 1 with the fixing element 6, among other things the need to insert a securing element into the intervertebral disc space, which could damage the end plates 8a of neighbouring vertebrae 8 in an undesired manner, is avoided. The position and orientation of the retaining portion 3 is defined by the fixing of the securing limb 2 on the vertebra 8. The height of the retaining portion 3 (measured between opposite end plates of neighbouring vertebrae 8) is in every case much smaller than the height of the intervertebral disc, which determines the distance between the end plates. It is thereby avoided that, after any further degeneration of the intervertebral disc 7, the implant or the retaining portion 3 comes into contact with the end plates of the vertebrae 8 on both sides and further restricts the mobility thereof and/or causes pain.

Figure 6:
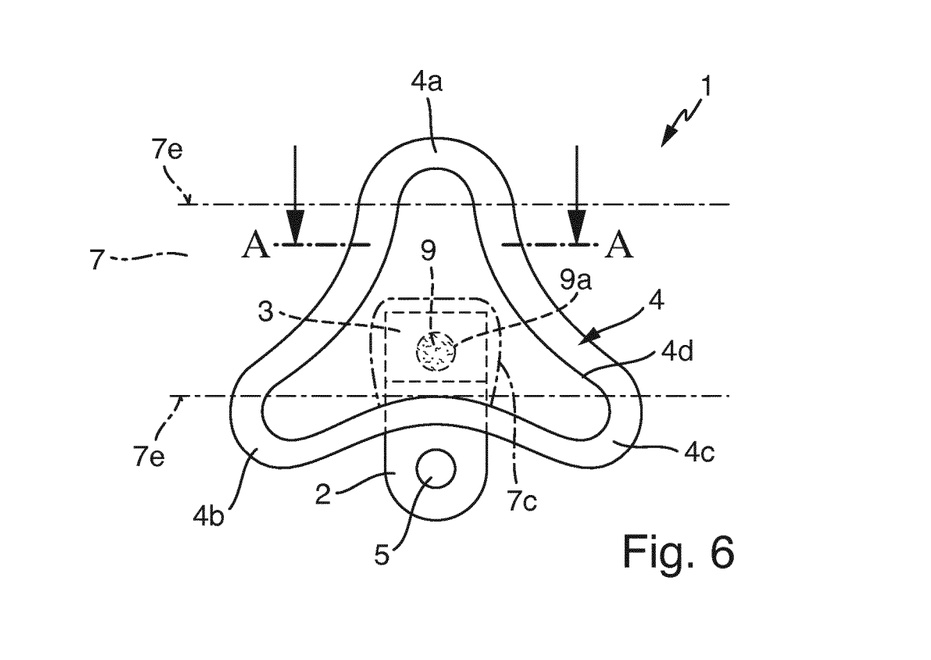
FIG. 6: a top view onto the inner side of an implant according to an embodiment of the present invention with a spread-out fothering.

An embodiment of an implant 1 of the present invention is shown in a top view onto the end face of the retaining portion 3 with a freely spread-out fothering 4 in FIG. 6. In the freely spread-out state, the fothering would extend beyond the upper and lower boundary planes of the intervertebral disc 7 indicated by dashed lines 7e. The prongs of the segments 4a, 4b and 4c are therefore bent after insertion such that they lie within the boundaries defined by the lines 7e. Of course, from the outset the fothering can also have smaller outer dimensions, which, in the freely spread-out state, lie within the expected boundary lines or have at least a smaller protrusion than represented here. The fothering 4 thus protrudes beyond the cross-sectional area of the retaining portion 3 and above all also beyond the cross section of a defect 7c in the top view onto the end face of the retaining portion 3. The fothering 4 is manufactured, in one piece, from PTFE.

Figure 6A:
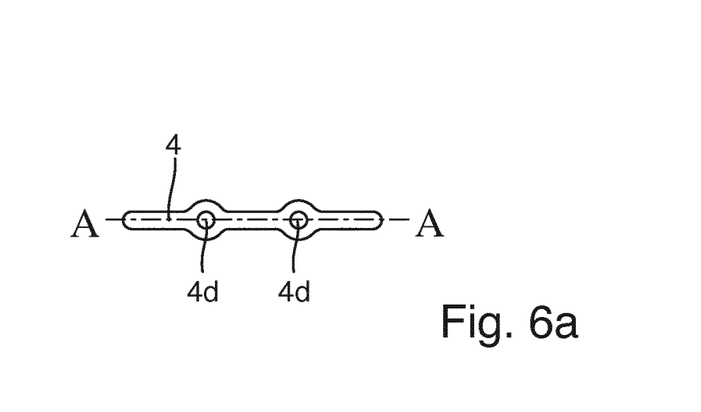
FIG. 6a: a superelevated cross section A-A through the fothering in FIG. 6.

For an automatic spreading-out of the fothering 4, pretensioned reinforcements 4d, e.g. made of spring steel, are incorporated into the fothering 4, as can be seen from the superelevated cross section, shown in FIG. 6a, through the fothering 4 along the line A-A. For example, the reinforcement 4d could consist of a ring-shaped wire which is forced into the shape represented in FIG. 4 and is thereby integrated into the fothering 4 under pretension, wherein the fothering 4 is additionally folded for introduction through the defect and spreads out to the represented shape after passing through the defect.

As is likewise indicated in FIG. 6, the securing limb 2 has an application port 9, which is formed as a perforable, elastic septum or a plug in a hole 9a extending lengthwise through the retaining portion 3. The hole 9a is sealed by the plug 9, with the result that a pointed hollow needle can pierce the plug 9 and then a flowable substance can be introduced into or drawn out of the inside of the intervertebral disc through the needle. After the hollow needle has been withdrawn, the pierced channel generated by the hollow needle automatically and completely seals itself because of the elasticity and internal adhesion of the plug material, wherein a hollow needle which, if possible, does not punch material out of the plug, but only dislodges the plug material is preferably used. In this way, for example, medicaments or therapeutic fluids can be introduced into the inside of the intervertebral disc without damaging the anulus fibrosus further. For diagnostic purposes as well, a fluid sample can be drawn from the inside of the intervertebral disc through the self-sealing plug.

Figure 7A:
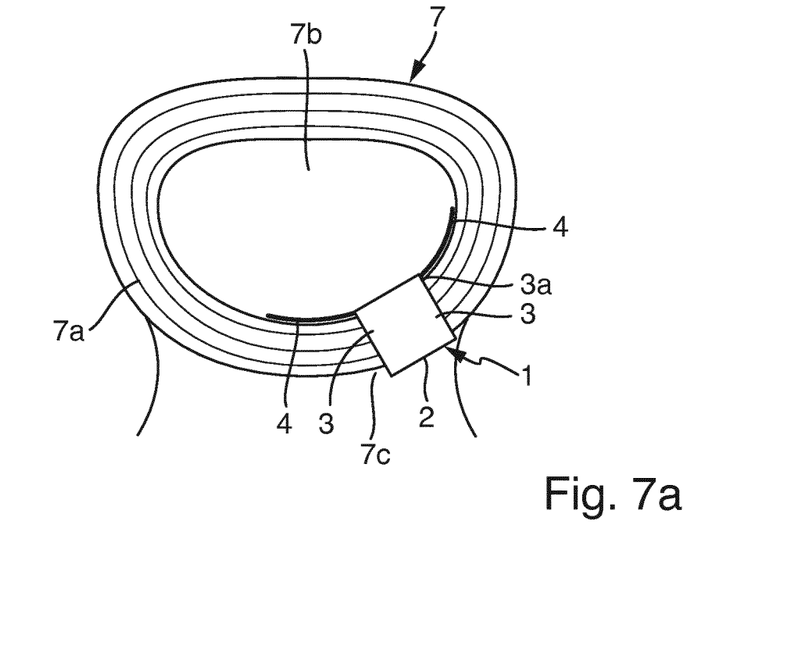
FIGS. 7a,b: the arrangement and position of the implant after introduction into an intervertebral disc.
Figure 7B:
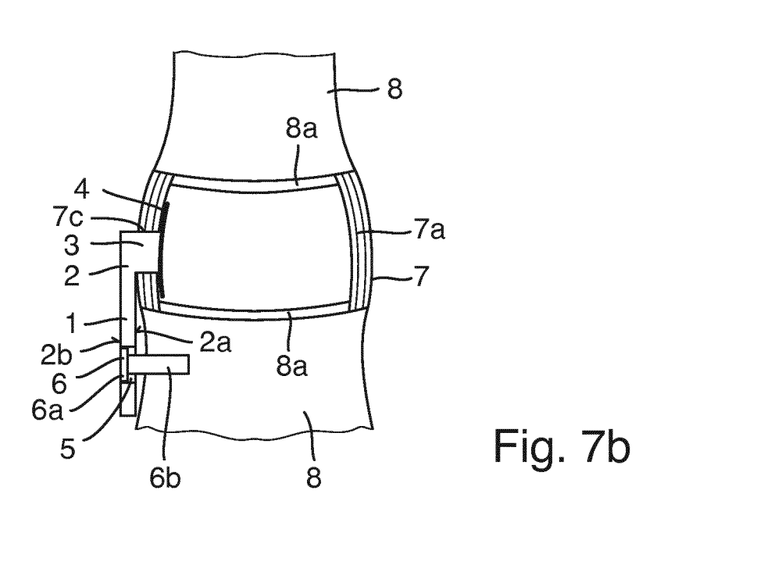

FIGS. 7a and 7b indicate the position of the implant introduced into an intervertebral disc in a horizontal and a vertical section. The fothering 4 rests against the inner side of the anulus fibrosus 7a and extends clearly beyond the cross section of the defect 7c. The retaining portion supports the fothering in the area of the defect 7c, at least until the fothering has taken or been incorporated. The retaining portion 3 and also the securing limb 2, as well as optionally also the fixing element 6, can consist of a material that can be resorbed by a patient's body.

Figure 8A:
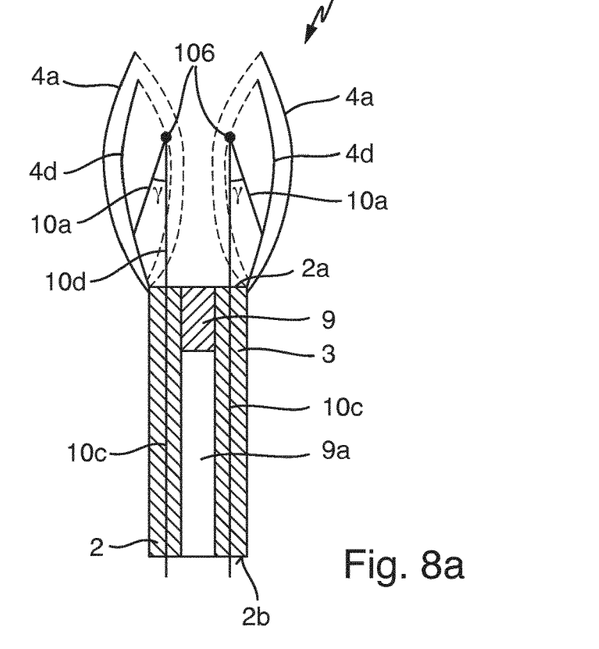
FIGS. 8a-c: side views of an implant according to the present invention with an unfolding mechanism, actuatable from outside, for a fothering in different unfolding states.
Figure 8B:
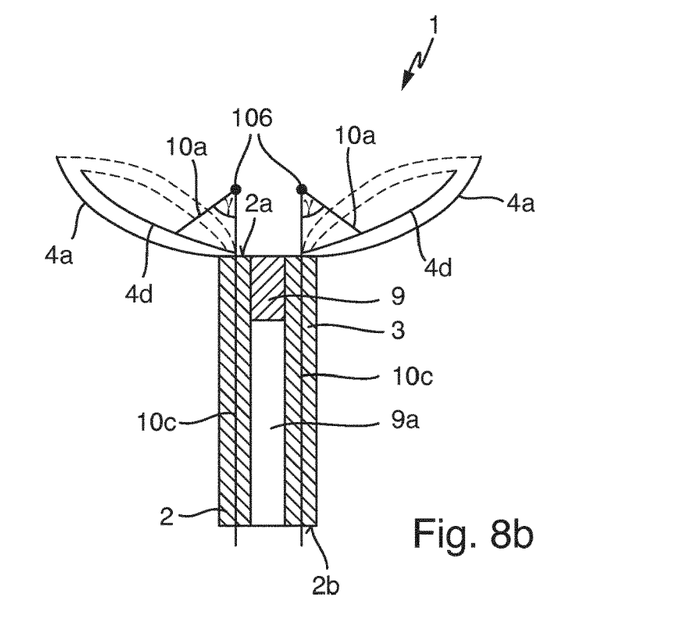
Figure 8C:
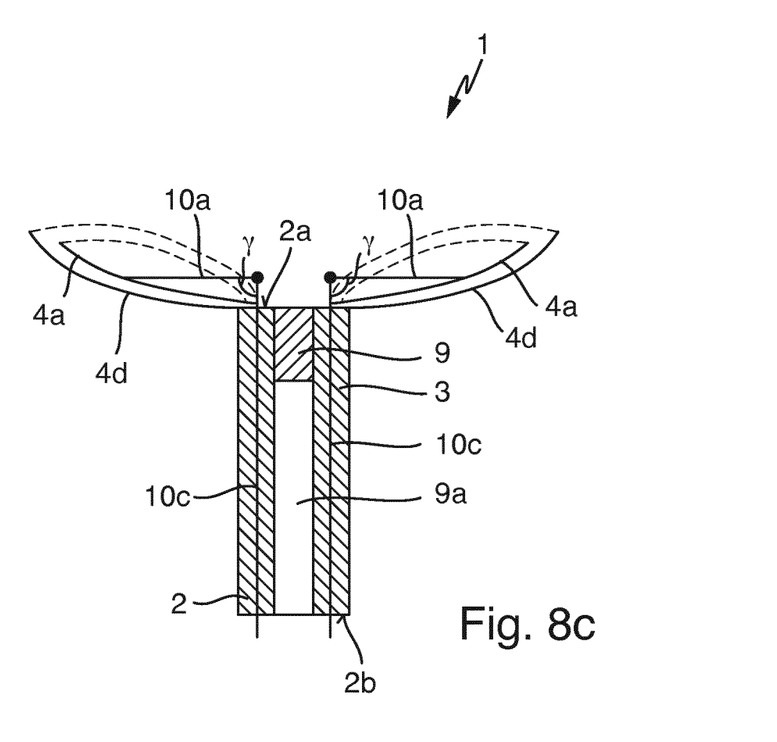

According to an embodiment of the present invention, an implant 1 is represented in a longitudinal section through the retaining portion 3 in FIGS. 8a-c. For the fothering 4, the implant 1 has an umbrella-like spreading-out mechanism 10a, 10b and a pull wire or thread 10c, which extends through the retaining portion 3 and one end of the securing limb 2 and is connected to two segments 4a (only indicated) of the fothering 4 such that the fothering 4 is spread out by a pull on the wire or thread 10c from the outer side 2b.

Each of the segments 4a has a reinforcement 4d, which is only indicated in FIG. 8 and which is connected, in each case with one strut 10a via an articulated connection 10b, to a pull rod 10d, the other end of which is connected to the pull thread or wire 10c. To illustrate the mode of operation of the spreading-out mechanism, the fothering 4 is represented in different opening positions in FIGS. 8a to 8c, wherein in FIG. 8a the fothering 4 is folded or closed, in FIG. 8b the fothering 4 is partially opened and in FIG. 8c the fothering is spread out completely. If the pull thread or wire is already held under pretension inside the defect 7c during introduction, the fothering unfolds as soon as it has passed through the defect 7c in the anulus fibrosus.

Figure 9A:
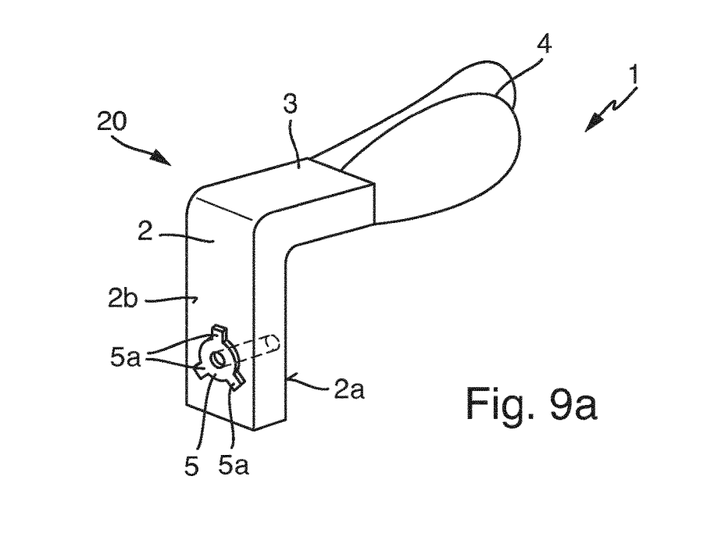
FIGS. 9a-c: an implant with a securing limb for the anti-twist receiving of fixing elements.
Figure 9B:
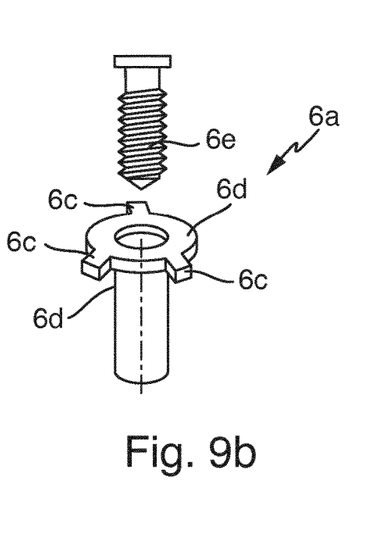
Figure 9C:
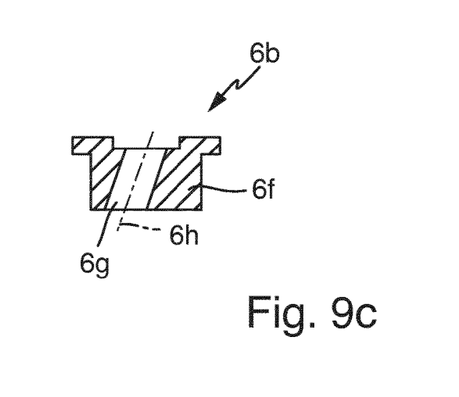

FIG. 9 shows a perspective view of a further embodiment of the present invention, in which the hole 5 in the securing limb 2 has positioning means in the form of edge recesses 5a which are arranged at spacings of 120° around a central hole. These edge recesses make it possible to receive a matching sleeve 6a, which has corresponding radial extensions 6c, and act as anti-twist protection for the sleeves 6a or 6b. Two corresponding sleeves 6a, 6b different from each other are represented in FIGS. 9b and 9c.

The edge recesses 5a and the radial extensions 6c make it possible to arrange the sleeves 6a, 6b in the central hole 5 in three different alignments, which is advantageous in particular when the sleeve itself has a hole 6g, the axis of which runs inclined relative to the axis 6h defined by the outer surface 6f of the sleeve 6a. The number and arrangement of the edge recesses 5a can, of course, be varied as desired in order to increase or reduce the number of possible orientations of the adapter sleeve 6a or 6b.

Fixing elements, such as for example screws, can thus be introduced into the vertebra from three different directions, depending on the alignment of the sleeve 6a and optionally a through hole through the sleeve, wherein the surgeon has the possibility of selecting the direction according to the smallest possible degree of injury to the bone parts and soft tissue lying on the path of access to the defect of the intervertebral disc. Alternatively, the edge recesses and extensions can act as anti-twist protection if, for example, the sleeve to be inserted into the hole 5 has a screw anchor lug 6d which extends into the bone material of the vertebra 8. A non-rotationally symmetrical screw head could also be secured against twisting with an additional sleeve, which is fitted onto the screw head on the one hand and at the same time locked into the hole 5 with the edge recesses 5a.

Examples of suitable sleeves 6a, 6b, such as can be used in some embodiments of the present invention for combination with an implant 1 according to the invention, are represented in FIGS. 9b and 9c.

For the purposes of original disclosure, it is pointed out that all features, as revealed to a person skilled in the art from the present description, the drawings and the claims, even if they were described specifically only in connection with particular further features, can be combined both individually and in any desired combinations with others of the features or feature groups disclosed here, unless this has been expressly ruled out or technical circumstances make such combinations impossible or pointless. The comprehensive, explicit representation of all conceivable combinations of features is dispensed with here only for the sake of the brevity and readability of the description.

LIST OF REFERENCE NUMBERS 1 implant
2 securing limb
2a inner side of the securing limb
2b outer side of the securing limb
3 retaining portion
3a end of the retaining portion
4 fothering
4 segment of the fothering
4b segment tip
4c longitudinal axis of the segment 4d reinforcement
5 hole for receiving a fixing element
5a positioning means, edge recess
6a sleeve
6b sleeve
6c extensions
6d screw anchor, screw anchor lug
6e screw, threaded shank
6f outer wall of the adapter sleeve
6g sleeve channel
6h longitudinal axis of the sleeve channel
7 intervertebral disc
7a anulus fibrosus
7b nucleus pulposus
7c defect
8 vertebra
8a end plate
9 application port, plug
9a through hole, hole
5 actuation means
10a strut
10b articulated connection
10c pull rod

The invention claimed is:

1. An implant for sealing a defect in an anulus fibrosus of an intervertebral disc, with a retaining portion for insertion into the defect, a flexible sealing element connected to an inner end of the retaining portion and a securing limb, connected to the outer end of the retaining portion, which is configured to be fixed to a vertebra adjoining the intervertebral disc, in order to hold the retaining portion in a fixed position, wherein the flexible sealing element has internal reinforcements, wherein the flexible sealing element has a reduced projected area in a top view from a front along a longitudinal axis of the retaining portion in a first state and has a widened projected area, which is at least twice the reduced projected area, in a second state, wherein the securing limb is angled relative to the longitudinal axis of the retaining portion and is arranged on the outer end of the retaining portion, which securing limb is configured to laterally contact a bony structure of the vertebra adjoining the intervertebral disc and configured to be secured to the vertebra with the aid of a fixing element which is movable relative to the securing limb.

2. The implant according to claim 1, wherein, at a distance from the retaining portion, the securing limb has a cross hole for the fixing element, to be anchored in the vertebra, to be guided through.

3. The implant according to claim 2, wherein the cross hole is inclined relative to the longitudinal direction of the retaining portion at an angle in a range of from 0° to 30°.

4. The implant according to claim 2, wherein an adapter sleeve is provided which can be inserted into the cross hole and which itself has a hole, the axis of which is inclined relative to a longitudinal axis of the cross hole at an angle in the range of from 0° to 30°.

5. The implant according to claim 4, wherein the adapter sleeve is pre-installable in the cross hole.

6. The implant according to claim 1, wherein the fixing element is selected from the group consisting of: a nail, a screw, a screw anchor with a screw and a secured screw with an expansion anchor.

7. The implant according to claim 1, wherein the securing limb and the retaining portion are formed in one piece.

8. The implant according to claim 1, wherein the securing limb and the retaining portion are connected to each other in a detachable manner.

9. The implant according to claim 1, wherein the securing limb and the retaining portion are connected to each other in an articulated manner.

10. The implant according to claim 1, wherein, on the inner end of the retaining portion, the sealing element is a fothering that can be spread out which projects beyond a cross-sectional area of the retaining portion on all sides in a top view onto an end face of the retaining portion in its spread-out state and is provided to seal the defect on an inner side of the anulus fibrosus.

11. The implant according to claim 10, wherein the fothering has integrated rod- or wire-shaped reinforcements, which either provide a pretension in the direction of the spread-out state or make it possible to spread out the fothering by manipulation of the reinforcements from outside.

12. The implant according to claim 10, wherein the fothering has at least two segments, wherein neighbouring segments are connected to each other at least in portions and/or overlap in portions in a spread-out state of the fothering.

13. The implant according to claim 10, wherein each segment of the fothering is designed leaf-shaped and has a longitudinal axis extending up to a leaf tip, and wherein the longitudinal axes of two neighbouring segments form an angle of from 10° to 120° in a spread-out state of the fothering.

14. The implant according to claim 10, wherein each segment of the fothering is designed leaf-shaped and has a longitudinal axis extending up to a leaf tip, and wherein the longitudinal axes of two neighbouring segments form an angle of from 45° to 90° in a spread-out state of the fothering.

15. The implant according to claim 10, wherein an actuation means, which is connected to the fothering and brings about the spreading-out of the fothering by actuation, is guided through the retaining portion from its outer to its inner end.

16. The implant according to claim 15, wherein the actuation means, together with reinforcements of the fothering, forms an inverse umbrella mechanism.

17. The implant according to claim 1, wherein the retaining portion has a through hole, extending from its outer to the inner end, which is sealed by an elastic, pierceable plug.

18. The implant according to claim 17, wherein the plug has a thickness of at least 2 mm in the direction of the through hole of the retaining portion.

19. The implant according to claim 1, wherein the securing limb is an elongate member extending transverse to the longitudinal axis of the retaining portion.

20. The implant according to claim 1, wherein the securing limb is selected from the group consisting of: a bar, a plate, or a strip.

* * * * *